US008637563B2

(12) United States Patent
Erickson-Miller

(10) Patent No.: US 8,637,563 B2
(45) Date of Patent: Jan. 28, 2014

(54) NON-PEPTIDE THROMBOPOIETIN RECEPTOR AGONIST IN THE TREATMENT OF CANCER AND PRE-CANCEROUS SYNDROMES

(75) Inventor: Connie Erickson-Miller, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/487,512

(22) Filed: Jun. 4, 2012

(65) Prior Publication Data

US 2012/0295918 A1 Nov. 22, 2012

Related U.S. Application Data

(63) Continuation of application No. 12/948,159, filed on Nov. 17, 2010, now abandoned, which is a continuation-in-part of application No. 12/166,686, filed on Jul. 2, 2008, now abandoned, which is a continuation-in-part of application No. PCT/US2008/054046, filed on Feb. 15, 2008.

(60) Provisional application No. 60/977,216, filed on Oct. 3, 2007, provisional application No. 60/969,192, filed on Aug. 31, 2007, provisional application No. 60/952,289, filed on Jul. 27, 2007, provisional application No. 60/949,347, filed on Jul. 12, 2007, provisional application No. 60/908,205, filed on Mar. 27, 2007, provisional application No. 60/892,552, filed on Mar. 2, 2007, provisional application No. 60/890,236, filed on Feb. 16, 2007.

(51) Int. Cl.
A01N 43/56 (2006.01)
A61K 31/415 (2006.01)

(52) U.S. Cl.
USPC ......................................................... 514/404

(58) Field of Classification Search
None
See application file for complete search history.

(56) References Cited

U.S. PATENT DOCUMENTS

| 5,342,947 | A | 8/1994 | Lacket et al. |
| 5,491,237 | A | 2/1996 | Fang et al. |
| 5,559,235 | A | 9/1996 | Luzzio et al. |
| 5,681,835 | A | 10/1997 | Willson |
| 5,877,219 | A | 3/1999 | Willson |
| 6,063,923 | A | 5/2000 | Fang et al. |
| 6,100,273 | A | 8/2000 | Besterman et al. |
| 6,207,716 | B1 | 3/2001 | Willson |
| 6,268,391 | B1 | 7/2001 | Dickerson et al. |
| 6,737,062 | B2 | 5/2004 | Nicolette |
| 6,887,890 | B2 | 5/2005 | Fujiwara et al. |
| 7,026,334 | B1 | 4/2006 | Takemoto et al. |
| 7,160,870 | B2 | 1/2007 | Duffy et al. |
| 7,314,887 | B2 | 1/2008 | Chen et al. |
| 7,547,719 | B2 | 6/2009 | Moore |
| 2003/0195231 | A1 | 10/2003 | Takemoto et al. |
| 2004/0053946 | A1 | 3/2004 | Lackey et al. |
| 2004/0077697 | A1 | 4/2004 | Koshio et al. |
| 2005/0153977 | A1 | 7/2005 | Sugasawa et al. |
| 2006/0116417 | A1 | 6/2006 | Chen et al. |
| 2007/0105824 | A1 | 5/2007 | Erickson-Miller et al. |
| 2007/0129539 | A1 | 6/2007 | Zhi et al. |

FOREIGN PATENT DOCUMENTS

| EP | 1 104 674 | 6/2001 |
| WO | WO99/22733 | 5/1999 |
| WO | WO 99/11262 | 11/1999 |
| WO | WO 01/89457 | * 11/2001 |
| WO | WO 02/59099 | 1/2002 |
| WO | WO 02/59100 | 1/2002 |
| WO | WO 03/062233 | * 7/2003 |
| WO | WO03/098992 | 12/2003 |
| WO | WO2004/096154 | 11/2004 |
| WO | WO2007/044982 | 4/2007 |
| WO | WO2007/062078 | 5/2007 |
| WO | WO2007/106564 | 9/2007 |
| WO | WO2008/073864 | 6/2008 |
| WO | WO2009/048953 | 4/2009 |
| WO | WO2009/151862 | 12/2009 |
| WO | WO2010/045310 | 4/2010 |

OTHER PUBLICATIONS

Walters et al. Mitoxantrone and high-dose cytosine arabinoside in refractory acute myelogenous leukemia. Cancer. 62: 677-682, 1988.*
Abraham, R. T., *Current Opinion in Immunology*, 8(3):412-8 (1996).
6,268,391.
Ashby, M.N., *Current Op. in Lipidology*, 9(2):99-102 (1998).
Balasubramanian, et al., *Cancer Letters*, 280:211-221 (2009).
Ball, Kathryn, *Progress in Cell Cycle Research*, 3:125-134 (1997).
Bertrand, Philippe, *European Journal of Medicinal Chemistry*, 45:2095-2116 (2010).
Bolen, et al., *Annual Review of Immunology*, 15:371-404 (1997).
Brekken, et al., *Cancer Research*, 60:5117-5124 (2000).
Brodt, et al., *Biochemical Pharm.*, 60:1101-1107 (2000).
Bruns, et al., *Cancer Research*, 60:2926-2935 (2000).
Canman, et al., *Oncogene*, 17(25):3301-3308 (1998). Chen, et al., *Blood*, 86:4054-4062 (1995).
Chen, et al., *Cancer Research*, 58:1965-1971 (1998).
Cwirla, *Science*, 276:1696 (1997).
Einzig, et al., *Proc. Am. Soc. Clin. Oncol.*, 20:46 (2001).
Ezumi, et al., *FEBS Letters*, 374:48-52 (1995).
Forastire, et al., *Sem. Oncol.*, 20:56 (1990).
Gauduchon, et al., *Clinical Cancer Research*, 11:2345-2354 (2005).
Giaccone, et al., *Int. J. Cancer*, 118:209-214 (2006).
Gottlicher, et al., *EMBO Journal*, 20(24):6969-6978 (2001).
Green, et al., *Cancer Treat. Rev.*, 26(4):269-286 (2000).
Greene, "Protective Groups in Organic Synthesis", 1981, Table of Contents.
Hasegawa, *Int. J. Immunopharm.*, 18:103-112 (1996).

(Continued)

Primary Examiner — Anna Pagonakis
(74) Attorney, Agent, or Firm — Wayne J. Dustman; Edward R. Gimmi

(57) ABSTRACT

Invented is a method of treating cancer or a pre-cancerous syndrome in a mammal, including a human, in need thereof which comprises the administration of an effective amount of a non-peptide thrombopoietin (TPO) receptor agonist to such mammal, suitably a human.

8 Claims, 4 Drawing Sheets

(56) References Cited

OTHER PUBLICATIONS

Holmes, et al., *J. Nat. Cancer Inst.*, 83:1797 (1991).
Jackson, S. P., *International Journal of Biochemistry and Cell Biology*, 29(7):935-8 (1997).
Kantarjian, et al., *Journal of Clinical Oncology*, 28:437-444 (2010).
Kojima, et al., *Thrombosis and Haemostasis*, 74:1541-1545 (1995).
Kath, John C., *Exp. Opin. Ther. Patents*, 10(6):803-818 (2000).
Kearns, et al., *Seminars in Oncology*, 3(6):16-23 (1995).
Kingston, et al., *Studies in Organic Chemistry*, 26:219-235 (1986).
Kitada, et al., *Antisense Res. Dev.*, 4:71-79 (1994).
Komatsu, *Blood*, 87:4552 (1996).
Kumar, *J. Biol. Chem.*, 256:10435-10441 (1981).
Kuter, et al., *Seminars in Hematology*, 37:41-49 (2000).
Lackey, K., et al., *Bioorganic and Medicinal Chemistry Letters*, 10:223-226 (2000).
Lamb, et al., *Nucleic Acids Research*, 23:3283-3289 (1995).
Laurenz, et al., *Comp. Biochem. & Phys., Part A Physiology*, 116:369-377 (1997).
Lofts, et al., *New Molecular Targets for Cancer Chem.*, 1994.
Markman, et al., *Yale Journal of Biology and Medicine*, 64:583 (1991).
Marks, et al., *Nature Biotechnology*, 25:84-90 (2007).
Martinez-Iacaci, L., et al., *Int. J. Cancer*, 88(1):44-52 (2000).
Massague, et al., *Cancer Surveys*, 27:41-64 (1996).
McCabe, et al., *Cancer Research*, 66:8109-8115 (2006).
McDonald, et al., *Am. J. of Pediatric Hematology/Oncology*, 1992, vol. 14, No. 1, pp. 8-21.
McGuire, et al., *Ann. Intern. Med.*, 111:273 (1989).
Metcalf, et al., *Nature*, Jun. 16, 1994, vol. 369, pp. 519-520.
Molina, et al., *Clin. Cancer Res.*, 14:23 (2008).
Panobinostat, *Drugs of the Future*, 32(4):315-322 (2007).
Philip, et al., *Cancer Treatment and Research*, 78:3-27 (1995).
Reilly, et al., *Cancer Research*, 60:3569-3576 (2000).
Richon, et al., *Proc. National Academy of Science*, 97:10014-10019 (2000).
Rosania, et al., *Exp. Opin. Ther. Patents*, 10(2):215-230 (2000).
Scharovsky, et al., *Journal of Biomedical Sciences*, 7(4):292-8 (2000).
Schiff, et al., *Proc. Natl. Acad. Sci.*, 77:1561-1565 (1980).
Schiff, et al., *Nature*, 277:665-667 (1979).
Schreiber, et al., *Science*, 232:1250-1253 (1986).
Seidel, *Proc. Natl. Acad. Sci. USA*, 92:3041-3045 (1995).
Shawyer, et al., *DDT*, 2(2):Feb. 1997.
Shiotsu, et al., *Exp. Hemat.*, 26:1195-1201 (1998).
Sinha, et al., *Journal of Hematotherapy and Stem Cell Res.*, 8(5):465-80 (1999).
Smithgall, T. E., *Journal of Pharmacological and Toxicological Methods*, 34(3):125-32 (1995).
Stenger, *Community Oncology*, 4:384-386 (2007).
Stern, *Breast Cancer Research*, 2:176-183 (2000).
Tefferi, *Mayo Clin. Proc.*, 85(11):1042-1045 (2010).
Vigon, *Proc. Natl. Acad. Sci. USA*, 89:5640-5644 (1992).
Vigushin, et al., *Anti-Cancer Drugs*, 13(1):1-13 (2002).
Vinodhkumar, et al., *Biomedicine & Pharmacotherapy*, 62:85-93 (2008).
Wani, et al., *J. Am. Chem. Soc.*, 93:2325 (1971).
Water, et al., *J. Clin. Oncol.*, 18:1812-1823 (2000).
Woo, et al., *Nature*, 368:750 (1994).
Yamamoto, et al., *Journal of Biochemistry*, 126(5):799-803 (1999).
Yen, et al., *Oncogene*, 19:3460-3469 (2000).
Zhelev, et al., *Cancer Chemotherapy Pharmacology*, 53:267-275 (2004).
Zhong, et al., *Cancer Res.*, 60(6):1541-1545 (2000).
Zhao, Jian-zeng, *Immunological Journal*, 16(4):S55-S58 (2000).
Zhao, Jian-zeng, *Immunological Journal*, English Translation 6(4):S55-S58 (2000).

\* cited by examiner

In Vitro response of CCRF-CEM Lymphoblastic T Cell Leukemia Cells Treated with Compound A in the Absence or Presence of rhTpo, rhEpo or rhG-CSF In Vitro Response of K562 Chronic Myelogenous Leukemia Cells treated with Compound A in the Absence or Presence of rhTpo, rhEpo or rhG-CSF In Vitro Response of MOLT-4 Acute Lyphoblastic T Cell Leukemia Cells Treated with Compound A in the Absence or Presence of rhTpo, rhEpo or rhG-CSF In Vitro Response of RPMI-8226 Plasmacytoma Cells Treated with Compound A in the Absence or Presence of rhTpo, rhEpo or rhG-CSF

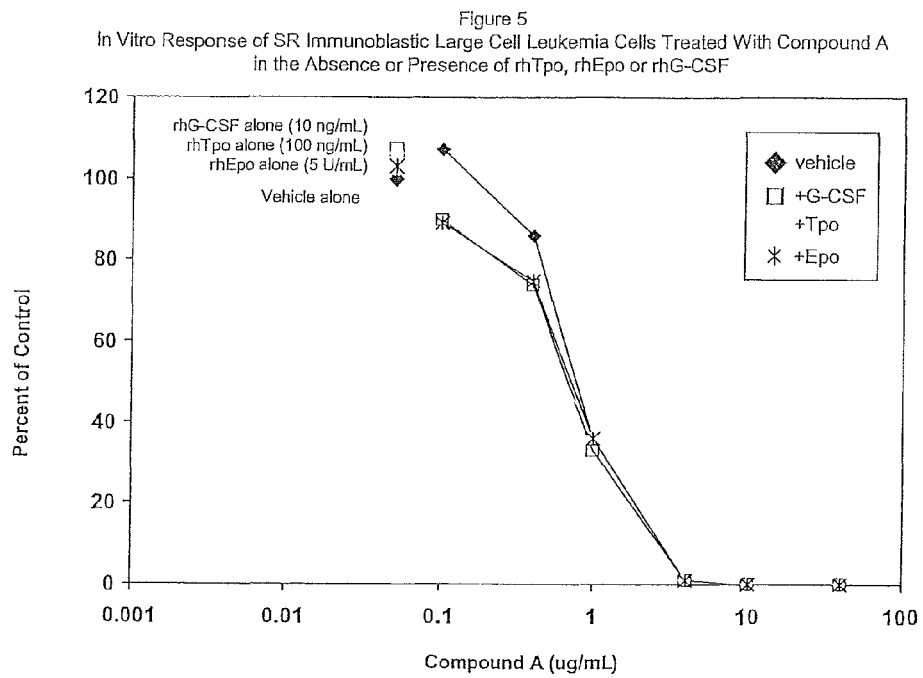
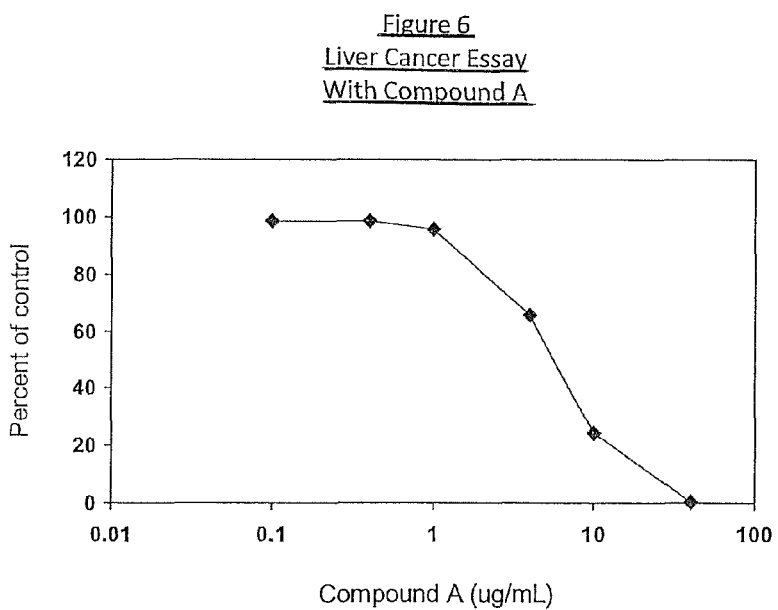

NON-PEPTIDE THROMBOPOIETIN RECEPTOR AGONIST IN THE TREATMENT OF CANCER AND PRE-CANCEROUS SYNDROMES

This application is a continuation of U.S. application Ser. No. 12/948,159, filed on Nov. 17, 2010, now abandoned which is a Continuation-in-Part of U.S. application Ser. No. 12/166,686, filed on Jul. 2, 2008, now abandoned which is a Continuation-in-Part of International Application No. PCT/US2008/054046 filed Feb. 15, 2008, which claims the benefit of U.S. Provisional Application Nos. 60/977,216 filed Oct. 3, 2007, 60/969,192 filed Aug. 31, 2007, 60/952,289 filed Jul. 27, 2007, 60/949,347 filed Jul. 12, 2007, 60/908,205 filed Mar. 27, 2007, 60/892,552 filed Mar. 2, 2007 and 60/890,236 filed Feb. 16, 2007.

FIELD OF THE INVENTION

This invention relates to a method of treating cancer and pre-cancerous syndromes in a mammal, including a human, in need thereof which comprises the administration of an effective amount of a combination of at least one non-peptide thrombopoietin (TPO) receptor agonist or TPO cell cycle activator and at least one chemotherapeutic agent to such mammal. Suitably, the method relates to methods of treating cancers and pre-cancerous syndromes by administration of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid and pharmaceutically acceptable salts, thereof, suitably the bis-(monoethanolamine) salt, (hereinafter the bis-(monoethanolamine) salt is Compound A and the corresponding salt free compound is Compound B) and at least one chemotherapeutic agent.

BACKGROUND OF THE INVENTION

Thrombopoietin (TPO) has been shown to be the main humoral regulator in situations involving thrombocytopenia. See, e.g., Metcalf Nature 369:519-520 (1994). TPO has been shown in several studies to increase platelet counts, increase platelet size, and increase isotope incorporation into platelets of recipient animals. Because platelets (thrombocytes) are necessary for blood clotting and when their numbers are very low a patient is at risk of death from catastrophic hemorrhage, TPO is considered to have potential useful applications in both the diagnosis and the treatment of various hematological disorders, for example, diseases primarily due to platelet defects. In addition, studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8-21 (1992).

The slow recovery of platelet levels in patients suffering from thrombocytopenia is a serious problem, and has lead to the search for small molecule non-peptide TPO receptor agonists that are able to accelerate platelet regeneration. (e.g. see, International Application Number PCT/US01/16863, having International Filing Date May 24, 2001, which specifically discloses Compound B, in Example 3, and the use of non-peptide TPO receptor agonists in combination with further active ingredients).

Compound A is disclosed in International Application No. PCT/US03/16255, having an International filing date of May 21, 2003; International Publication Number WO 03/098002 and an International Publication date of Dec. 4, 2003.

Non-peptide TPO receptor agonists, including Compound A, are disclosed for the treatment of degenerative diseases/injuries in International Application No. PCT/US04/013468, having an International filing date of Apr. 29, 2004; International Publication Number WO 04/096154 and an International Publication date of Nov. 11, 2004.

Formulations containing Compound A, suitably at 12.5 mg, 25 mg, 50 mg, 75 mg, and 100 mg tablets based on weight of the free or unsalted compound, are disclosed in International Application No. PCT/US2007/074918, having an International filing date of Aug. 1, 2007, International Publication Number WO 08/136843 and an International Publication date of Nov. 13, 2008, which is incorporated herein by reference.

The present invention concerns novel therapeutic uses of known classes of compounds, non-peptide TPO receptor agonists and TPO cell cycle activators.

SUMMARY OF THE INVENTION

This invention relates to a method of treating cancer in a mammal, including a human, in need thereof which comprises administering to such mammal a therapeutically effective amount of a non-peptide TPO receptor agonist or a TPO cell cycle activator and at least one chemotherapeutic agent.

This invention relates to a method of treating pre-cancerous syndromes in a mammal, including a human, in need thereof which comprises administering to such mammal a therapeutically effective amount of a non-peptide TPO receptor agonist or a TPO cell cycle activator and at least one chemotherapeutic agent.

Included among the non-peptide TPO receptor agonists of the invention are compounds of Formula (I):

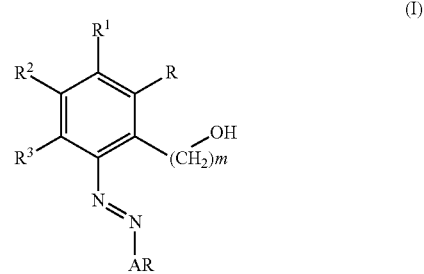

(I)

wherein:
R, $R^1$, $R^2$ and $R^3$ are each independently selected from hydrogen, $C_{1-6}$alkyl, $-(CH_2)_pOR^4$, $-C(O)OR^4$, formyl, nitro, cyano, halogen, aryl, substituted aryl, substituted alkyl, $-S(O)_nR^4$, cycloalkyl, $-NR^5R^6$, protected $-OH$, $-CONR^5R^6$, phosphonic acid, sulfonic acid, phosphinic acid, $-SO_2NR^5R^6$, and a heterocyclic methylene substituent as represented by Formula (III),

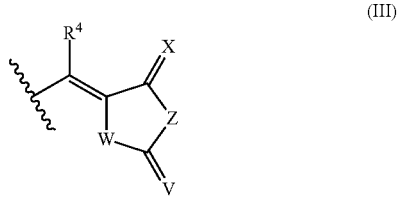

(III)

where, p is 0-6, n is 0-2,

V, W, X and Z are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

m is 0-6; and

AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$_n$R$^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

and pharmaceutically acceptable salts thereof;

provided that at least one of R, $R^1$, $R^2$ and $R^3$ is a substituted aryl group or a heterocyclic methylene substituent as represented in Formula (III).

This invention relates to a method of treating cancer in a mammal, including a human, in need thereof which comprises administering to such mammal a therapeutically effective amount of a non-peptide TPO receptor agonist of Formula (I) and at least one chemotherapeutic agent.

This invention relates to a method of treating pre-cancerous syndromes in a mammal, including a human, in need thereof which comprises administering to such mammal a therapeutically effective amount of a non-peptide TPO receptor agonist of Formula (I) and at least one chemotherapeutic agent.

Included in the present invention are pharmaceutical compositions comprising a pharmaceutical carrier and compounds useful in the methods of the invention.

Also included in the present invention are methods of co-administering the combinations of the present invention with further active ingredients.

BRIEF DESCRIPTION OF THE DRAWINGS

FIG. 5 shows the in vitro response of SR Immunoblastic Large Cell Leukemia cells treated with Compound A.

FIG. 6 shows the in vitro response of HepG2 cells treated with Compound A.

DETAILED DESCRIPTION OF THE INVENTION

Figure 1:
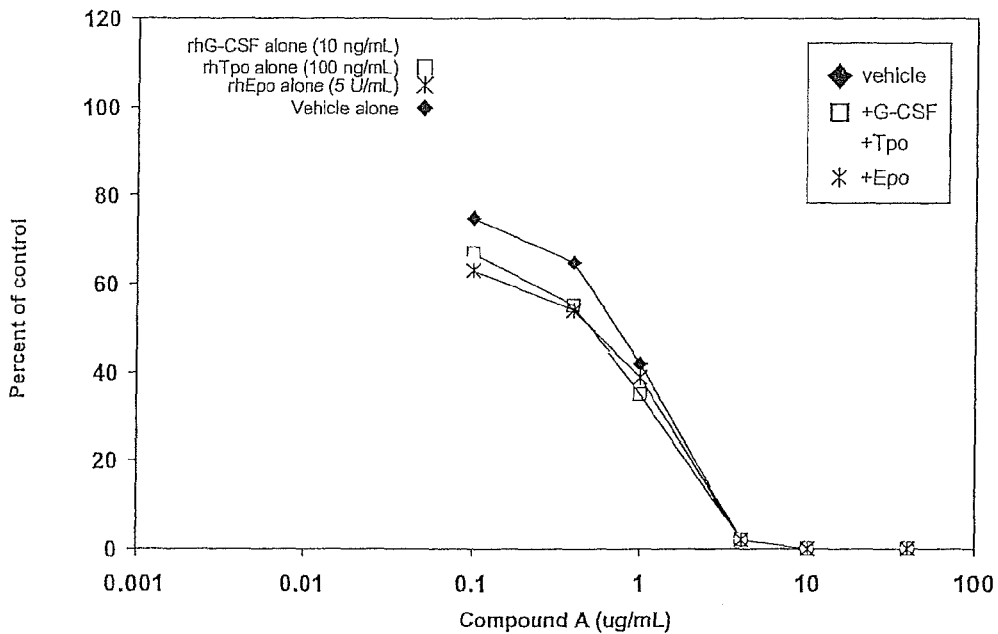
FIG. 1 shows the in vitro response of CCRF-CEM Lymphoblastic T cell leukemia cells treated with Compound A.

This invention relates to methods of treating cancer and pre-cancerous syndromes in a mammal, including a human, in need thereof which comprises administering to such mammal a therapeutically effective amount of a non-peptide TPO receptor agonist, including compounds of Formula (I) as described herein, or a TPO cell cycle activator and at least one chemotherapeutic agent to such mammal.

Suitably, the invention relates to a method of treating cancer in a mammal, including a human, wherein the cancer is selected from: brain (gliomas), glioblastomas, astrocytomas, glioblastoma multiforme, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Suitably, the invention relates to a method of treating cancer in a mammal, including a human, wherein the cancer is selected from: Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute megakaryocytic leukemia, and Erythroleukemia.

Suitably, the invention relates to a method of treating cancer in a mammal, including a human, wherein the cancer is selected from: malignant lymphoma, hodgkins lymphoma, non-hodgkins lymphoma, lymphoblastic T cell lymphoma, Burkitt's lymphoma and follicular lymphoma.

Suitably, the invention relates to a method of treating cancer in a mammal, including a human, wherein the cancer is selected from: neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the invention relates to a method of treating pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis (especially viral induced hepatitis), all of which can progress to cancer.

Included among compounds of Formula (I) that are useful in the current invention are those having Formula (VI):

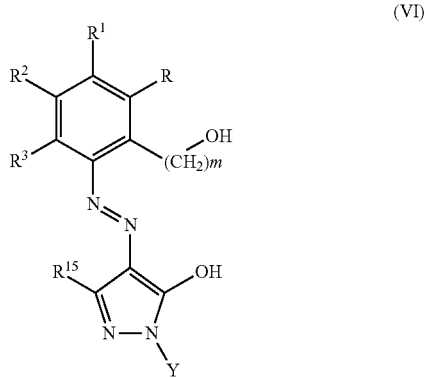

(VI)

wherein:
R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid and —$SO_2NR^5R^6$, where
p is 0-6,
n is 0-2,
$R^4$ is hydrogen, alkyl, cycloalkyl, $C_1$-$C_{12}$aryl, substituted alkyl, substituted cycloalkyl and substituted $C_1$-$C_{12}$aryl, and
$R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;
$R^{15}$ is selected from the group consisting of alkyl, $C_1$-$C_{12}$aryl, hydroxy, alkoxy, substituted alkyl, substituted $C_1$-$C_{12}$aryl and halogen;
m is 0-6; and
Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, $C_1$-$C_{12}$aryl, substituted cycloalkyl, substituted $C_1$-$C_{12}$aryl, hydroxy, aryloxy, alkoxy, cycloalkyl, nitro, cyano, halogen and protected —OH;
and pharmaceutically acceptable salts, thereof;
provided that at least one of R, $R^1$, $R^2$ and $R^3$ is a substituted aryl group.

Included among the compounds useful in the present invention are those having Formula (VI) in which, either:

R is a substituted aryl; and $R^1$ is hydrogen;
or:
R is hydrogen; and $R^1$ is a substituted aryl;
and in either case:
$R^2$ and $R^3$ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;
$R^{15}$ is selected from the group consisting of alkyl, substituted alkyl, $C_{1-12}$aryl, alkoxy and halogen;
m is 0-4; and
Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts thereof.

Included among the compounds useful in the present invention are those having Formula (VI) in which,
R is a substituted $C_1$-$C_{12}$aryl;
and
$R^1$ is hydrogen;
$R^2$ and $R^3$ are each independently selected from hydrogen, $C_{1-6}$alkyl, $C_{1-6}$alkoxy, nitro, cyano, halogen, substituted alkyl and cycloalkyl;
$R^{15}$ is selected from the group consisting of alkyl, substituted alkyl, $C_1$-$C_{12}$aryl, alkoxy and halogen;
m is 0-2; and
Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts thereof.

Included among the compounds useful in the present invention are those having Formula (VI) in which,
R is a substituted phenyl or pyridinyl ring; and
$R^1$ is hydrogen;
$R^2$ and $R^3$ are each independently selected from hydrogen, $C_{1-6}$alkyl, substituted alkyl and halogen;
$R^{15}$ is selected from the group consisting of $C_{1-4}$alkyl, $C_{1-4}$alkoxy, $C_1$-$C_{12}$aryl and halogen;
m is 0; and
Y is selected from,
phenyl, pyridinyl and pyrimidinyl, where the phenyl, pyridinyl and pyrimidinyl is optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts thereof.

Included among the compounds useful in the present invention are:
3'-{N'-[1-(3,4-Dimethylphenyl)-3-methyl-5-oxo-1,5-dihydropyrazol-4-ylidene]hydrazino}-2'-hydroxybiphenyl-3-carboxylic acid;
3-{N'-[1-(3,4-dimethylphenyl)-3-methyl-5-oxo-1,5-dihydropyrazol-4-ylidene]hydrazino}-2-hydroxy-3'-(tetrazol-5-yl)biphenyl;
1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid;

3'-{N'-[1-(3,5-Dimethyl-phenyl)-2-oxo-6-trifluoromethyl-1,2-dihydro-indol-3-ylidene]-hydrazino}-2'-hydroxybiphenyl-3-carboxylic acid;

2'-hydroxy-3'-{N'-[2-oxo-1-(4-propyl-phenyl)-1,2-dihydro-indol-3-ylidene]-hydrazino}-biphenyl-4-carboxylic acid; and and pharmaceutically acceptable salts thereof.

Included among the non-peptide TPO receptor agonists of the invention are the non-peptide compounds described in:
WO 02/59099;
WO 02/59100;
EP 1 207 155;
EP 1 253 142A1;
WO 01/92211 A1;
WO 01/53267-A1;
WO 03/62233
WO 02/62775
EP 1 104 674-A1; and
WO 01/07423-A1.

Included among the compounds of the above listed applications that are useful in the present invention are:
N-[4-(5-bromo-2-thienyl)-1,3-thiazol-2-yl]-4-[(Z)-(2,4-dioxo-1,3-thiazolidin-5-ylidene)methyl]benzamide;
N-[4-(3,4-dimethylphenyl)-1,3-thiazol-2-yl]-4-[(Z)-(2,4-dioxo-1,3-thiazolidin-5-ylidene)methyl]benzamide;
N-{4-[4-(1,1-dimethylethyl)phenyl]-1,3-thiazol-2-yl}-4-[(Z)-(2,4-dioxo-1,3-thiazolidin-5-ylidene)methyl]benzamide;
N-[4-(3,4-dichlorophenyl)-1,3-thiazol-2-yl]-4-[(Z)-(2,4-dioxo-1,3-thiazolidin-5-ylidene)methyl]benzamide; and
(2E)-3-[4-({[4-(3,4-dichlorophenyl)-1,3-thiazol-2-yl]amino}carbonyl)phenyl]-2-methyl-2-propenoic acid;
and/or pharmaceutically acceptable salts thereof.

Included among the non-peptide TPO receptor agonists of the invention are the non-peptide compounds described in:
WO 99/11262.

Included among the non-peptide TPO receptor agonists of the invention are the non-peptide compounds described in:
International Application No. PCT/US05/018924, having an International filing date of May 27, 2005; International Publication Number WO 05/118551 and an International Publication date of Dec. 15, 2005, International Application No. PCT/US05/038055, having an International filing date of Oct. 21, 2005; International Publication Number WO 06/047344 and an International Publication date of May 4, 2006, International Application No. PCT/US06/045129, having an International filing date of Nov. 21, 2006; International Publication Number WO 07/062078 and an International Publication date of May 31, 2007, and International Application No. PCT/US07/006547, having an International filing date of Mar. 14, 2007; International Publication Number WO 07/106564 and an International Publication date of Sep. 20, 2007.

The compounds that are final products in WO 05/118551, WO 06/047344, WO 07/062078 and WO 07/106564 are useful in the present invention, these compounds are included herein by reference.

The compound that is the product of Example 4 in WO 07/106564, 3'-{N'-[1-(3,5-Dimethyl-phenyl)-2-oxo-6-trifluoromethyl-1,2-dihydro-indol-3-ylidene]-hydrazino}-2'-hydroxybiphenyl-3-carboxylic acid, as the salt free compound or in the form of a pharmaceutically acceptable salt, hydrate, solvate or ester, is a compound useful in the present invention.

The compound that is the product of Example 6 in WO 07/106564, 2'-hydroxy-3'-{N'-[2-oxo-1-(4-propyl-phenyl)-1,2-dihydro-indol-3-ylidene]-hydrazino}-biphenyl-4-carboxylic acid, as the salt free compound or in the form of a pharmaceutically acceptable salt, hydrate, solvate or ester, is a compound useful in the present invention.

Included among the non-peptide TPO receptor agonists of the invention is the non-peptide compound described in:
International Application No. PCT/JP03/012419, having an International filing date of Sep. 29, 2003; International Publication Number WO 04/029049 and an International Publication date of Apr. 8, 2004, 2005.

The compound that is the final product in WO 04/029049, both the salt and non-salt forms, is useful in the present invention, these compounds are included herein by reference.

Suitably, the compound that is the final product in WO 04/029049 is 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, as the salt free compound (hereinafter Compound E), or in the form of a pharmaceutically acceptable salt hydrate solvate or ester thereof. Suitably, the salt is a maleic acid salt (hereinafter Compound F). The structure of Compound F is indicated below.

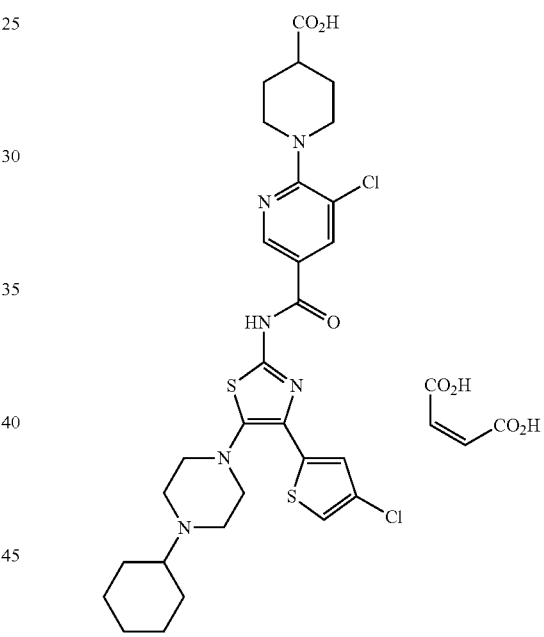

Non-peptide TPO receptor agonists are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$-$C_{12}$aryl"as used herein, unless otherwise defined, is meant phenyl naphthalene, 3,4-methylenedioxyphenyl pyridine, biphenyl, quinoline, pyrimidine, quinazoline, thiophene, furan, pyrrole, pyrazole, imidazole and tetrazole.

When referring to compounds of Formula (I) and (II), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_nR^8$, nitro, tetrazole, cyano, oxo, halogen, trifluoromethyl, protected -OH and a heterocyclic methylene substituent as represented by Formula (III),

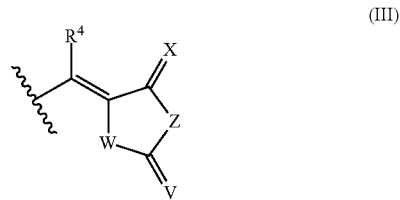

(III)

where g is 0-6; $R^8$ is hydrogen or alkyl; $R^{20}$ is selected form hydrogen, $C_1$-$C_4$alkyl, aryl and trifluoromethyl; $R^{21}$ and $R^{22}$ are independently selected form hydrogen, $C_1$-$C_4$alkyl, aryl and trifluoromethyl; V, W, X and Z are each independently selected from O, S, and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl; and n is 0-2.

When referring to compounds of Formula (V) and (VI), the term "substituted"as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_nR^8$, nitro, tetrazole, cyano, oxo, halogen, trifluoromethyl and protected -OH, where g is 0-6, $R^8$ is hydrogen or alkyl, $R^{20}$ is selected form hydrogen, $C_1$-$C_4$alkyl, aryl and trifluoromethyl, and $R^{21}$ and $R^{22}$ are independently selected form hydrogen, $C_1$-$C_4$alkyl, aryl and trifluoromethyl, and n is 0-2.

By the term "alkoxy" as used herein is meant —O-alkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$-$C_{12}$.

Examples of cycloalkyl and substituted cycloalkyl substituents as used herein include: cyclohexyl, 4-hydroxy-cyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O) alkyl where alkyl is as described herein. Examples of acyloxy substituents as used herein include: —$OC(O)CH_3$, —$OC(O) CH(CH_3)_2$ and —$OC(O)(CH_2)_3CH_3$.

By the term "N-acylamino" as used herein is meant —N(H)C(O)alkyl, where alkyl is as described herein.

Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —O-aryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —$(CH_2)_gC(O)OR^8$, —$S(O)_nR^8$, nitro, cyano, halogen and protected —OH, where g is 0-6, $R^8$ is hydrogen or alkyl, and n is 0-2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$, —$CH(CH_3)$—$CH_2$—$CH_3$, —$CH$=$CH_2$, and —$C$≡$C$—$CH_3$.

By the term "treating" and derivatives thereof as used herein, is meant prophylatic and therapeutic therapy. Prophylactic therapy is appropriate, for example, when a subject is considered at high risk for developing cancer, such as when a subject has a strong family history of cancer, or when a subject has been exposed to a carcinogen.

Prophylactic use of the compounds of this invention is contemplated whenever numerous causative factors are present in a subject. Prophylactic uses of the methods of this invention include but are not limited to treatment of heavy smokers with no detectable cancer or when a subject has been exposed to high levels radiation.

By the phrases "to a therapeutic extent", "treating" and "therapeutically effective amount" and derivatives thereof as used herein, unless otherwise defined, is meant that amount of the presently invented combination that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, lessening in severity or amelioration of cancer.

Cancer is known to have many causative factors. This invention relates to the treatment of cancer regardless of the factor or factors causing the condition. The pharmaceutically active combinations of this invention are also useful in treating cancer when the causative factor or factors of the condition are unknown or have yet to be identified.

A skilled physician will be able to determine the appropriate situation in which subjects are susceptible to or at risk of, for example, lung cancer for administration by methods of the present invention.

By the phrase "non-peptide" as used herein is meant a chemical compound, or a protein or peptide not comprised primarily of natural amino acids. Suitably, the "non-peptide" is a small molecule chemical compound having a molecular weight under 1,500 daltons, suitably under 1,000 daltons.

By the term "primarily" as used above is meant about 60% by weight of naturally occurring amino acid residue.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of the compounds of the invention.

Certain compounds described herein may form a solvate which is understood to be a complex of variable stoichiometry formed by a solute (for example, a compound of Formula I of a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

The compounds of the invention are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COON, and acetate maleate and the like for —OH, and those esters known in the art for modifying solubility or hydrolysis characteristics, for use as sustained release or prodrug formulations.

The pharmaceutically acceptable salts of the compounds of the invention are readily prepared by those of skill in the art.

The compounds of Formula I are disclosed and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001, the entire disclosure of which is hereby incorporated by reference. Compounds of Formulas I and pharmaceutically acceptable salts, hydrates, solvates and esters thereof, are prepared as described in International Application No. PCT/US01/16863. The bis-(monoethanolamine) salt of a compound described in International Application No. PCT/US01/16863, is described in International Application No. PCT/US03/16255, having an International filing date of May 21, 2003; International Publication Number WO 03/098992 and an International Publication date of Dec. 4, 2003.

It is known that certain cancers, particularly various types of leukemia, are unresponsive to treatment with chemotherapeutic agents. One reason attributed to this phenomenon is the unresponsiveness of noncycling cells, such as leukemic cells in resting $G_0$ phase, to cell cycle-dependent cytotoxic agents such as chemotherapeutic agents. Synchronized recruitment of leukemic cells into activated phases of the cell cycle activating cytokine (granulocyte-macrophage colony-stimulating factor) [GM-CSF] has resulted in significant increased sensitivity to cytotoxic agents. Experimental Hematology 32 (2004) 188-194.

In one embodiment of this invention, TPO (thrombopoietin) directed peptides which bind the TPO receptor as described in U.S. Pat. Nos. 5,869,451; 5,932,546; 6,083,913; 6,121,238; 5,869,451; 6,251,864; 6,506,362 and 6,465,430 as well as TPO modified with polyethylene glycol, TPO modified by glycosylation as described by Elliot, et al. (Nature Biotechnology 21:414-421, 2003) and AMG531 (Amgen, Thousand Oaks, Calif.) (discussed in N. Engl. J. Med. 2006; 355; 1672-1681) (hereinafter collectively referred to, unless otherwise defined, as TPO cell cycle activator(s)), suitably for use herein the TPO cell cycle activator is AMG531, are used in combination with chemotherapeutic agents, examples of chemotherapeutic agents for use in this invention include: gemcitabine, carboplatin, cisplatin, cytarabine, thalidomide, lenolidomide (Revlimid®) and decitabine, to treat cancers which are known to enter noncycling cell phases, particularly various types of leukemia, such as Lymphoblastic T cell leukemia, Chronic myelogenous leukemia, Chronic lymphocytic leukemia, Hairy-cell leukemia, acute lymphoblastic leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute myelogenous leukemia (AML), promyelocytic leukemia, acute megakaryocytic leukemia, and Erythroleukemia. Additional compounds for use in combination with TPO cell cycle activator, suitably AMG531, as described herein are disclosed in Tefferi, Mayo Clin. Proc. November 2010; 85(11): 1042-1045.

In one embodiment of this invention, non-peptide TPO receptor agonist; suitably Compound A, suitably Compound B, suitably Compound C, suitably Compound D; are used in combination with chemotherapeutic agents, examples of chemotherapeutic agents for use in this invention include: gemcitabine, carboplatin, cisplatin, cytarabine, thalidomide, lenolidomide (Revlimid®) and decitabine, to treat cancer, suitably cancers which are known to enter noncycling cell phases, particularly various types of leukemia, such as Lymphoblastic T cell leukemia, Chronic myelogenous leukemia, Chronic lymphocytic leukemia, Hairy-cell leukemia, acute lymphoblastic leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute myelogenous leukemia (AML), promyelocytic leukemia, acute megakaryocytic leukemia, and Erythroleukemia. Additional compounds for use in combination with a non-peptide TPO receptor agonist; suitably Compound A, suitably Compound B, suitably Compound C, suitably Compound D; as described herein are disclosed in Tefferi, Mayo Clin. Proc. November 2010; 85(11): 1042-1045.

The treatment of cancer, as described herein, is accomplished by the administration of a non-peptide TPO receptor agonist or TPO cell cycle activator and at least one chemotherapeutic agent and is not limited to any particular mechanism of action.

The treatment of pre-cancerous syndromes, as described herein, is accomplished by the administration of a non-peptide TPO receptor agonist or TPO cell cycle activator and at least one chemotherapeutic agent and is not limited to any particular mechanism of action.

When referring to the treatment of pre-cancerous syndromes, the term "co-administering" and derivatives thereof as used herein is meant either simultaneous administration or any manner of separate sequential administration of a non-peptide TPO receptor agonist, as described herein, or TPO cell cycle activator and at least one chemotherapeutic agent, and a further active ingredient or ingredients, known to be useful in the treatment of pre-cancerous syndromes. The term further active ingredient or ingredients, as used herein, includes any compound or therapeutic agent known to or that demonstrates advantageous properties when administered to a patient in need of treatment for pre-cancerous syndromes. Preferably, if the administration is not simultaneous, the compounds are administered in a close time proximity to each other. Furthermore, it does not matter if the compounds are administered in the same dosage form, e.g. one compound may be administered topically and another compound may be administered orally.

When referring to the treatment of cancer, the term "co-administering" and derivatives thereof as used herein is meant either simultaneous administration or any manner of separate sequential administration of a non-peptide TPO receptor agonist, as described herein, or TPO cell cycle activator and at least one chemotherapeutic agent and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the combinations of the current invention are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of Streptomyces verticillus, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

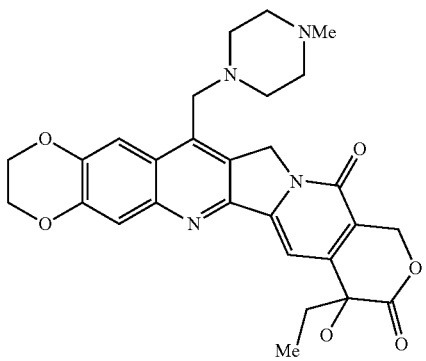

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotheraphy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin erbB2 antibody (see Tyrosine Kinase Signalling in Breast cancer: erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) or a pharmaceutically acceptable salt thereof at least one chemotherapeutic agent and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

The current invention relates to the use of a non-peptide thrombopoietin (TPO) receptor agonist or a TPO cell cycle activator and at least one chemotherapeutic agent in the treatment of pre-cancerous syndromes in mammals, including humans.

The current invention relates to the use of a non-peptide thrombopoietin (TPO) receptor agonist or a TPO cell cycle activator and at least one chemotherapeutic agent in the treatment of cancer in mammals, including humans.

TPO is known to have various effects including anti-apotitic/survival effects on megakaryocytes, platelets and stem cells, and proliferative effects on stem cells and megakaryocytic cells (Kuter D. J. Seminars in Hematology, 2000, 37, 41-9). These TPO activities effectively increase the number of stem and progenitor cells so that there is synergistic effects when TPO is used in conjunction with other cytokines that induce differentiation.

The non-peptide TPO receptor agonists of the current invention are also useful in acting on cells for survival and/or proliferation in conjunction with other agents known to act on cells for survival and/or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.,* 1997, 116, 369-77), FK23 (Hasegawa T., et al. *Int. J. Immunopharm.,* 1996, 18 103-112) and other molecules identified as having anti-apoptotic, survival or proliferative properties for stem cells, progenitor cells, or other cells expressing TPO Receptors.

One skilled in the art can readily determine by known methods if a compound is a non-peptide TPO receptor agonist and thus included within the scope of the current invention. By way of example, the following assays can be employed:

Luciferase Assay

Compounds are tested for potency as agonists of the TPO receptor in a Luciferase assay such as described in Lamb, et al., *Nucleic Acids Research* 23: 3283-3289 (1995) and Seidel, et al., *Proc. Natl. Acad. Sci., USA* 92: 3041-3045 (1995) by substituting a TPO-responsive BaF3 cell line (Vigon et al. *Proc. Natl. Acad. Sci. USA* 1992, 89, 5640-5644) for the HepG2 cells utilized therein. The murine BaF3 cells express TPO receptors and closely match the pattern of STAT (signal transducers and activators of transcription) activation observed in primary murine and human bone marrow cells.

Proliferation Assay

Compounds are tested in an in vitro proliferation assay using the human UT7TPO cell line. UT7TPO cells are a human megakaryoblastic cell line that express Tpo-R, whose survival and growth is dependent on the presence of TPO (Komatsu et al. *Blood* 1996, 87, 4552).

Differentiation Assay

Compounds are tested for their ability in stimulating the maturation of megakaryocytes from human bone marrow cells. In this assay, purified human CD34+ progenitor cells are incubated in liquid culture with test compounds for 10 days and the number of cells expressing the transmembrane glycoprotein CD41 (gpIIb), a megakaryocytic marker, is then measured by flow cytometry (see Cwirla, S. E. et al *Science,* 1997, 276, 1696).

The ability of non-peptide TPO receptor agonists to treat cancer is demonstrated by activity in the following Assays.

Cancer Proliferation Assay

Flat-bottom 96-well microtiter tissue culture plates (Costar, Cambridge, Mass.) were used for the assay. Cultures were performed in replicates of 4 wells; each well contained $1 \times 10^4$ cells. Six concentrations of Compound A (ranging from 40 µg/mL to 100 ng/mL) were tested in the absence and presence of 10 ng/mL G-CSF, 100 ng/mL of TPO or 5 U/mL of EPO. Cells were also tested in medium alone, G-CSF alone, TPO alone, or EPO alone to establish 100% of control values. The final volume in each well was 200 µL. Plates were placed in a humidified 5% $CO_2$ incubator at 37° C. for 3 days. Proliferation was measured by the uptake of tritiated thymidine ($^3$H-TdR) by pulsing wells with 1 µCi of $^3$H-TdR for the final 18 hours of incubation, harvesting the plate on a Brandel 96-well cell harvester (Gaithersburg, Md.) and measuring radioactivity on the filter mats in a Wallac 1450 Microbeta TriLux scintillation counter (Turku, Finland). The effect of Compound A was determined by comparing the results of cells treated with test compound with control cells (100% of control).

| Cell Line | Description | Compound A IC50 (ug/mL) |
|---|---|---|
| CCRF-CEM | Lymphoblastic T cell leukemia | 0.74 |
| K562 | Chronic myelogenous leukemia | 1.80 |
| MOLT-4 | Acute lymphoblastic T cell leukemia | 0.56 |
| RPMI-8226 | Plasmacytoma | 5.90 |
| SR | Immunoblastic large cell leukemia | 0.77 |

Figure 2:
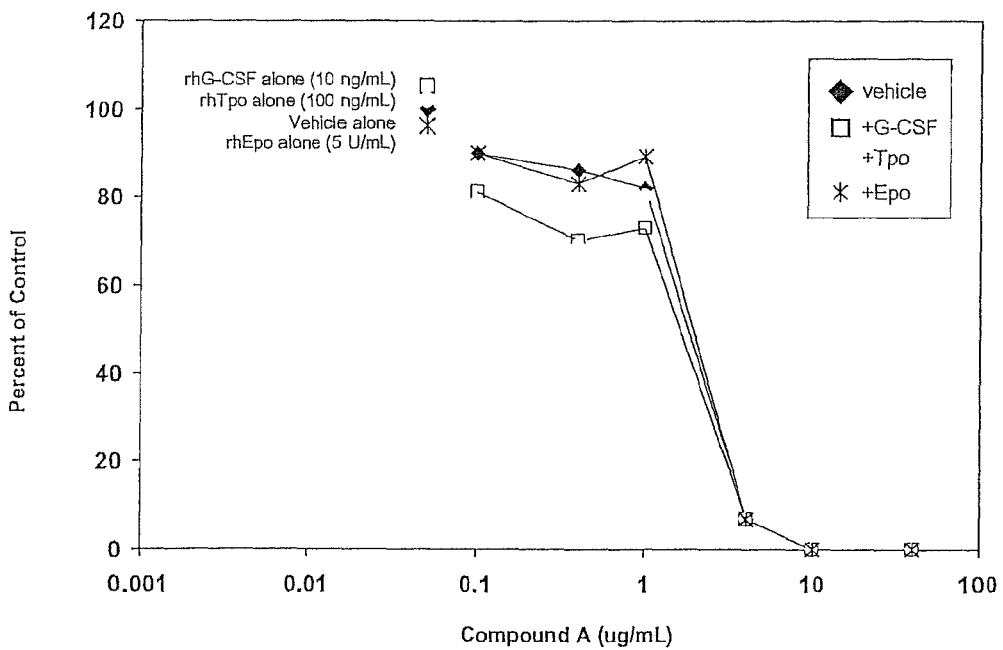
FIG. 2 shows the in vitro response of K562 Chronic Myelogenous leukemia cells treated with Compound A.
Figure 3:
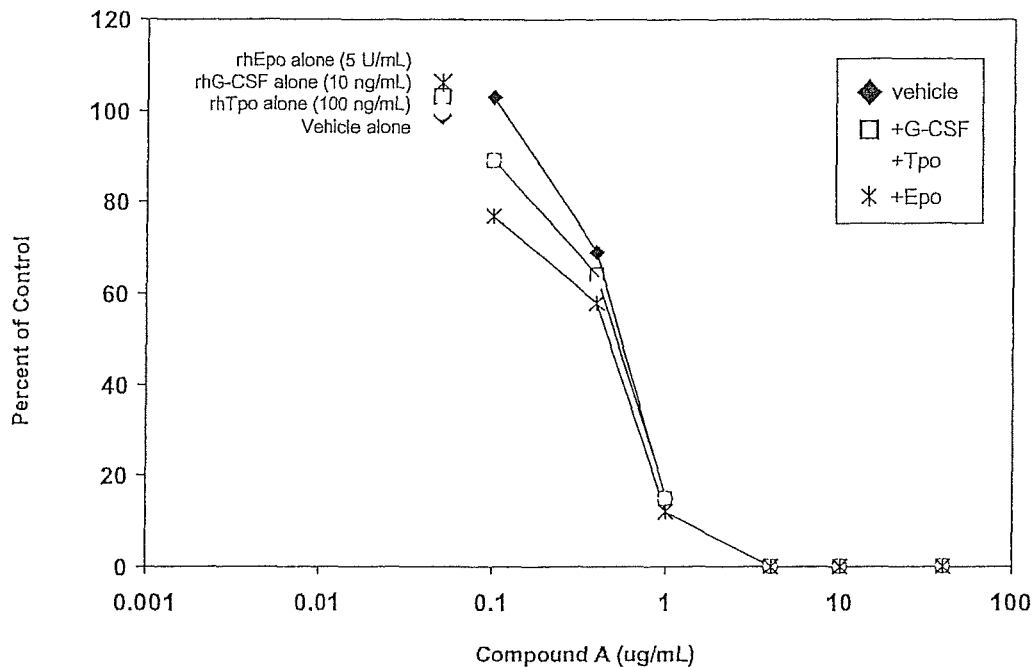
FIG. 3 shows the in vitro response of MOLT-4 Acute Lymphoblastic T cell leukemia cells treated with Compound A.
Figure 4:
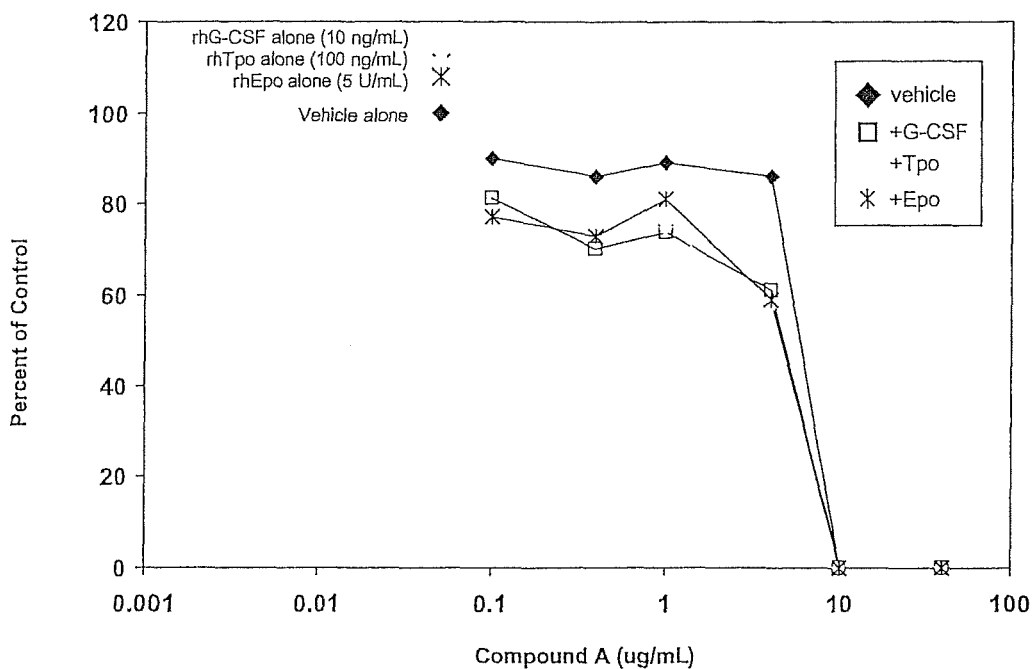
FIG. 4 shows the in vitro response of RPMI-8226 Plasmacytoma cells treated with Compound A.
Figure 7:
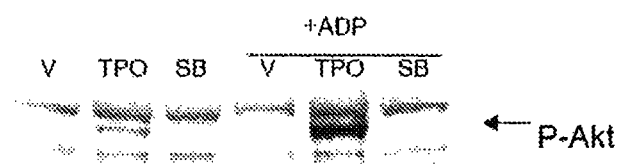
FIG. 7 shows the activation of Akt in human platelets treated with TPO or Compound A.

See FIGS. 1 to 5

Activation of Akt in Human Platelets Treated with TPO or Compound A

Washed human platelets from healthy volunteers were treated with vehicle (V) [0.33% DMSO], 100 ng/mL TPO [recombinant human thrombopoietin obtained from R&D Systems, Inc., Minneapolis, Minn., USA, or SB (SB=Compound A in Blot 1) (10 mM) for 15 minutes alone, or 13 minutes alone followed by 2 minutes with 1 mM ADP (+ADP). Protein extracts were probed for Akt (Ser473) activation. Results are representative of 3 individual experiments.

Compound A was compared to TPO in human platelets through the examination of a signal transduction pathway known to be activated through TPOR [TPO receptor] stimulation; specifically, Pi3K/Akt pathway activation [Chen, J., et al., Blood, 86, 4054-4062 (1995); Kojima, H., et al., Thrombosis & Haemostassis, 74, 1541-1545 (1995); Ezumi, Y., et al., FEBS Letters, 374, 48-52 (1995)]. Treatment of washed platelet preparations with TPO (Blot 1) resulted in significant Akt activation, as demonstrated through the use of phosphorylation-specific antibodies directed against Akt. However, no activation was observed when Compound A was used (termed SB in Blot 1). In addition, preincubation with TPO resulted in the significant enhancement of activation of Akt in combination with ADP (1 µM) as compared to TPO or ADP alone (no activation observed). Further, on enhanced activation was observed when platelets were incubated with Compound A prior to addition of ADP.

These results indicate that TPOR stimulation by the non-peptide TPO receptor agonist, Compound A, did not result in Akt phoshorylation, where stimulation by TPO did result in Akt phoshorylation. Because Akt activity is implicated in certain cancers, these results provide one possible explanation for the anti cancer activity of non-peptide TPO receptor agonist generally and specifically Compound A.

Liver Cancer Assay

HepG2 is a human hepatocellular carcinoma cell line. Active cell determinations were performed on HepG2 cells by plating $2 \times 10^4$ cells/mL in 96-well plates in culture medium containing 10% FBS and incubating overnight in 5% CO2 at 37°. Cells were then treated with Compound A at 0, 0.1, 0.4, 1, 4, 10, 40 ug/mL and incubated for 72 hours. Cell proliferation was measured using the CellTiter Glo (Promega) reagent according to the manufacturer's protocol. Data is the mean of n=4 wells reported as the percent of the control (0 ug/mL of Compound A).

Compound A induced a decrease in the number of viable cells with an IC50 of approximately 6 ug/mL.

See FIG. 6

Solid Tumor Cell Line Proliferation Assays
Cell Titer Glo Methodology:
Cells in log phase growth were seeded in a 96-well plate at 2500 cells/well in 50 uL medium and incubated at 37° C., 5% $CO_2$ overnight. Compound A was diluted in medium and added at 0.1, 0.4, 1, 4, 10 and 40 ug/mL. Following a 72 hr incubation at 37° C., 5% $CO_2$. The CellTiter-Glo Luminescent Cell Viability Assay (ProMega Corp) was performed according to the manufacturer's instructions. Briefly following a 30 min room temperature incubation 100 uL CELLTiter Glo reagent was added to each well and mixed for 2 minutes. Luminescence was recorded following a 10 minute room temperature incubation using a PerkinElmer Microbeta luminescence counter. IC50 was determined by EXCel Fit 4.2.1. The effect of Compound A is indicated in the table below.

| Cell line | Cell type | IC50 (µg/mL) | Assay Format |
| --- | --- | --- | --- |
| NCI-H23 | NSCLC | 13.9 | Cell Titer Glo |
| HOP-92 | NSCLC | 13.5 | Cell Titer Glo |
| EKVX | NSCLC | 12.7 | Cell Titer Glo |
| NCI-H226 | NSCLC | 11.0 | Cell Titer Glo |
| HOP-62 | NSCLC | 10.6 | Cell Titer Glo |
| A549 | NSCLC | 9.10 | Cell Titer Glo |
| NCI-H322M | NSCLC | 8.30 | Cell Titer Glo |
| NCI-H522 | NSCLC | 5.90 | Cell Titer Glo |
| NCI-H460 | NSCLC | 5.70 | Cell Titer Glo |
| HepG2 | Hepatocellular carcinoma | 5.61 | Cell Titer Glo |

References describing Cell Titer glo Methodology include the following:
Zhelev et al, Cancer Chemother Pharmacol 2004: 53:267-275; McCabe, et al (2006) *Cancer Res.* 66, 8109-8115; and Gauduchon, et al (2005) *Clin. Cancer Res.* 11, 2345-2354.

The combinations of the present invention are tested for efficacy, advantageous and synergistic properties according to known procedures such as described in, Molina et al., Clin. Cancer Res 2008; 14(23) Dec. 1, 2008 and Giaccone et al, Int. J. Canc: 118, 209-214 (2006), both of which are incorporated herein by reference.

The administration of a therapeutically effective amount of the combinations of the invention are advantageous over the individual component compounds in that the combinations will provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

Many current treatments for cancer and precancerous syndromes are toxic to the patient and/or are known to trigger adverse events which require the patient to stop the treatment periodically in order to recover from the toxic effects and/or to allow the adverse events to subside. This recovery period also provides the cancer or precancerous syndrome the opportunity to re-establish. One advantage of the combinations of the invention, is that the non-peptide TPO receptor agonists, suitably a compound selected from the following:

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

1-(3-chloro-5-{[4-(4-chlorothiophen-2-yl)-5-(4-cyclohexylpiperazin-1-yl)thiazol-2-yl]carbamoyl}pyridin-2-yl)piperidine-4-carboxylic acid;

3'-{N'-[1-(3,5-Dimethyl-phenyl)-2-oxo-6-trifluoromethyl-1,2-dihydro-indol-3-ylidene]-hydrazino}-2'-hydroxybiphenyl-3-carboxylic acid; and 2'-hydroxy-3'-{N'-[2-oxo-1-(4-propyl-phenyl)-1,2-dihydro-indol-3-ylidene]-hydrazino}-biphenyl-4-carboxylic acid;
or a pharmaceutically acceptable salt thereof, or
the TPO cell cycle activator,
in combination with at least one chemotherapeutic agent,
is that the combination is considered generally less toxic than standard anticancer therapies and are capable of being administered on a daily basis over a long period of time, suitably for over two weeks, suitably for over one month, suitably for over three months, suitably for over six months, suitably for over nine months, suitably for over a year, suitably chronic administration thereby providing continuous treatment of the cancer or precancerous syndrome. This advantage in the treatment of cancer and precancerous syndromes can be realized whether the combination is being administered alone or whether another anti-neoplastic agent is being co-administered. Even when the co-administered anti-neoplastic agent is periodically stopped, one or more agents of the combination can continue to be administered in order to provide sustained treatment of the cancer or precancerous syndrome.

The present invention therefore provides a method of treating cancer in a mammal, including a human, including wherein the cancer is selected from: brain (gliomas), glioblastomas, astrocytomas, glioblastoma multiforme, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute megakaryocytic leukemia, and Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer,
which comprises the administration an effective amount of at least one non-peptide thrombopoietin (TPO) receptor agonist or TPO cell cycle activator and at least one chemotherapeutic agent to a mammal, including a human, in need thereof.

The present invention therefore provides a method of treating pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis,
which comprises the administration an effective amount of at least one non-peptide thrombopoietin (TPO) receptor agonist or TPO cell cycle activator and at least one chemotherapeutic agent to a mammal, including a human, in need thereof.

The individual agents of the combinations may be administered to a patient in need thereof by any conventional route of administration, including, but not limited to, intravenous, intramuscular, oral, subcutaneous, intradermal, and parenteral.

The individual agents of the combinations of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the individual agents of the combinations of the present invention in a pharmaceutical dosage unit or units as described above will be an efficacious, nontoxic quantity preferably selected from the range of 0.001-100 mg/kg of active compound, preferably 0.002-50 mg/kg. When treating a human patient in need of a combination of the invention, each selected dose is administered preferably from 1-6 times daily, orally or parenterally. Preferred forms of parenteral administration include topically, rectally, transdermally, by injection and continuously by infusion. Oral dosage units for human administration suitably contain from 0.05 to 3500 mg, suitably from 0.1 to 3000 mg, suitably from 10 to 200 mg of each active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular agent or agents in use, the strength of the preparation, the mode of administration, and the advancement of the disease condition. Additional factors depending on the particular patient being treated will result in a need to adjust dosages, including patient age, weight, diet, and time of administration.

The method of this invention of treating cancer in mammals, including humans, comprises administering to a subject in need thereof a therapeutically effective amount of a pharmaceutically active combination of the present invention.

The present invention relates to the use of a non-peptide thrombopoietin (TPO) receptor agonist or TPO cell cycle activator and at least one chemotherapeutic agent in the treatment of cancer in a mammal, including a human.

The present invention relates to the in vivo administration of a combination of a non-peptide thrombopoietin (TPO) receptor agonist or TPO cell cycle activator and at least one chemotherapeutic agent in the treatment of cancer in a mammal, including a human.

The invention also provides for the use of a combination of a non-peptide thrombopoietin (TPO) receptor agonist or TPO cell cycle activator and at least one chemotherapeutic agent in the manufacture of a medicament for use in therapy.

The invention also provides for a pharmaceutical composition for use in the treatment of cancer which comprises a combination of a non-peptide thrombopoietin (TPO) receptor agonist or TPO cell cycle activator and at least one chemotherapeutic agent and a pharmaceutically acceptable carrier or carriers.

The method of this invention of treating pre-cancerous syndromes in mammals, including humans, comprises administering to a subject in need thereof a therapeutically effective amount of a combination of a non-peptide thrombopoietin (TPO) receptor agonist or TPO cell cycle activator and at least one chemotherapeutic agent of the present invention.

The present invention relates to the use of a combination of a non-peptide thrombopoietin (TPO) receptor agonist or TPO cell cycle activator and at least one chemotherapeutic agent in the treatment of pre-cancerous syndromes in a mammal, including a human.

The present invention relates to the in vivo administration of a combination of a non-peptide thrombopoietin (TPO) receptor agonist or TPO cell cycle activator and at least one chemotherapeutic agent in the treatment of pre-cancerous syndromes in a mammal, including a human.

The invention also provides for the use of a combination of a non-peptide thrombopoietin (TPO) receptor agonist or TPO cell cycle activator and at least one chemotherapeutic agent in the manufacture of a medicament for use in the treatment of pre-cancerous syndromes in mammals including humans.

The invention also provides for a pharmaceutical composition for use in the treatment of pre-cancerous syndromes which comprises a combination of a non-peptide thrombopoietin (TPO) receptor agonist or TPO cell cycle activator and at least one chemotherapeutic agent and a pharmaceutically acceptable carrier or carriers.

The invention also provides for the use of a combination of a non-peptide thrombopoietin (TPO) receptor agonist or TPO cell cycle activator and at least one chemotherapeutic agent in the manufacture of a medicament for use in the treatment of pre-cancerous syndromes.

In addition, the pharmaceutically active combinations of the present invention can be co-administered with further active ingredients, such as other compounds known to treat cancer.

In addition, the pharmaceutically active combinations of the present invention can be co-administered with further active ingredients, such as other compounds known to treat pre-cancerous syndromes.

Contemplated Equivalents—It will be appreciated by the person of ordinary skill in the art that the compounds of Formulas I and VI may also exist in tautomeric forms. For example, in Formula I, the double bond that is drawn between the two nitrogen atoms exists between the lower nitrogen atom and the AR substituent. Tautomeric forms of the compounds of Formulas I and VI are exemplified by the following Formula (X):

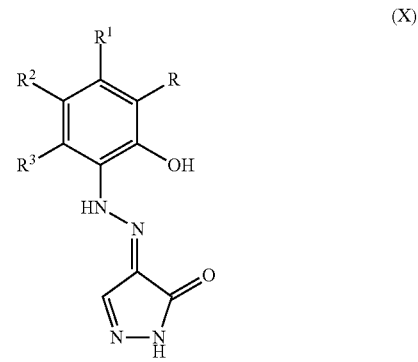

where the 'R' groups are as defined above. All such compounds are included in the scope of the invention and inherently included in the definition of the compounds of Formulas I and VI.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

Capsule Composition

An oral dosage form for administering an agent of the present invention is produced by filing a standard two piece hard gelatin capsule with the ingredients in the proportions shown in Table I, below.

TABLE I

| INGREDIENTS | AMOUNTS |
| --- | --- |
| 3'-{N'-[1-(3,4-Dimethylphenyl)-3-methyl-5-oxo-1,5-dihydropyrazol-4-ylidene]hydrazino}-2'-hydroxybiphenyl-3-carboxylic acid | 25 mg |
| Mannitol | 55 mg |
| Talc | 16 mg |
| Magnesium Stearate | 4 mg |

Example 2

Injectable Parenteral Composition

An injectable form for administering an agent of the present invention is produced by stirring 1.5% by weight of 3-{N'-[1-(3,4-dimethylphenyl)-3-methyl-5-oxo-1,5-dihydropyrazol-4-ylidene]hydrazino}-2-hydroxy-3'-(tetrazol-5-yl)biphenyl, in 10% by volume propylene glycol in water.

Example 3

Tablet Composition

The sucrose, microcrystalline cellulose and a non-peptide TPO agonist, as shown in Table II below, are mixed and granulated in the proportions shown with a 10% gelatin solution. The wet granules are screened, dried, mixed with the starch, talc and stearic acid, then screened and compressed into a tablet containing one agent of the present invention.

TABLE II

| INGREDIENTS | AMOUNTS |
| --- | --- |
| 3'-{N'-[1-(3,4-Dimethylphenyl)-3-methyl-5-oxo-1,5-dihydropyrazol-4-ylidene]hydrazino}-2'-hydroxybiphenyl-3-carboxylic acid | 20 mg |
| Microcrystalline cellulose | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating acute myelogenous leukemia (AML) in a mammal in need thereof which comprises the administration of a therapeutically effective amount of a compound selected from:
   3'-{N'-[1-(3,4-Dimethylphenyl)-3-methyl-5-oxo-1,5-dihydropyrazol-4-ylidene]hydrazino}-2'-hydroxybiphenyl-3-carboxylic acid;
   3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl; and
   1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid;
or a pharmaceutically acceptable salt thereof wherein said mammal is not suffering from thrombocytopenia.

2. The method according to claim 1 wherein the mammal is a human.

3. The method according to claim 2 wherein the compound is administered orally.

4. The method according to claim 2 wherein the compound is administered parenterally.

5. The method according to claim 3 wherein the compound is:
   3'-{N'-[1-(3,4-Dimethylphenyl)-3-methyl-5-oxo-1,5-dihydropyrazol-4-ylidene]hydrazino}-2'-hydroxybiphenyl-3-carboxylic acid;
or a pharmaceutically acceptable salt thereof.

6. The method according to claim 5 wherein the compound is:
   3'-{N'-[1-(3,4-Dimethylphenyl)-3-methyl-5-oxo-1,5-dihydropyrazol-4-ylidene]hydrazino}-2'-hydroxybiphenyl-3-carboxylic acid bis-(monoethanolamine).

7. The method according to claim 3 wherein the compound is:
   3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;
or a pharmaceutically acceptable salt thereof.

8. The method according to claim 3 wherein the compound is:
   1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid;
or a pharmaceutically acceptable salt thereof.

* * * * *